(12) United States Patent  
Gellibert

(10) Patent No.: US 7,157,479 B2  
(45) Date of Patent: Jan. 2, 2007

(54) OXAZOL/THIAZOL-DERIVATIVES ACTIVATORS OF THE HPPAR-ALPHA RECEPTOR

(75) Inventor: Francoise Jeanne Gellibert, Les Ulis (FR)

(73) Assignee: Glaxo Group Limited, Middlesex (GB)

( * ) Notice: Subject to any disclaimer, the term of this patent is extended or adjusted under 35 U.S.C. 154(b) by 0 days.

(21) Appl. No.: 10/478,936

(22) PCT Filed: May 29, 2002

(86) PCT No.: PCT/EP02/05886

§ 371 (c)(1),  
(2), (4) Date: May 10, 2004

(87) PCT Pub. No.: WO02/096895

PCT Pub. Date: Dec. 5, 2002

(65) Prior Publication Data

US 2005/0070517 A1    Mar. 31, 2005

(30) Foreign Application Priority Data

May 31, 2001  (GB) ................................. 0113231.5

(51) Int. Cl.  
*A61K 31/426*   (2006.01)  
*C07D 277/30*   (2006.01)  
(52) U.S. Cl. ............... 514/365; 514/374; 548/200; 548/236  
(58) Field of Classification Search ........... 548/200, 548/236; 514/365, 374  
See application file for complete search history.

(56) References Cited

U.S. PATENT DOCUMENTS 6,518,290 B1* 2/2003 Sierra .................. 514/365  
6,867,225 B1* 3/2005 Dumaitre et al. .......... 514/365

FOREIGN PATENT DOCUMENTS

| EP | 0 930 299 | 7/1999 |
| EP | 1 067 109 | 1/2001 |
| WO | WO 00/64876 | 11/2000 |
| WO | WO 01/00603 | 1/2001 |
| WO | WO 01/16120 | 3/2001 |
| WO | WO-01/40207 A1 * | 6/2001 |

OTHER PUBLICATIONS

Moreno et al., Journal of the American College of Cardiology (2004), vol. 44, No. 12, pp. 2293-2300.*  
Forman, B.M., et al. Hypolipidemic Drugs, Polyunsaturated Fatty Acids, And Eicosanoids Are Ligands For Peroxisome Proliferator-Activated Receptors Alpha and Delta. Proceedings of the National Academy of Sciences of USA, National Academy of Science. Washington, US, vol. 94, Apr. 1997, pp. 4312-4317.

* cited by examiner

*Primary Examiner*—Laura L. Stockton  
(74) *Attorney, Agent, or Firm*—Jennifer L. Fox

(57) ABSTRACT

A compound of formula (I) and pharmaceutically acceptable salts, solvates and hydrolysable esters thereof

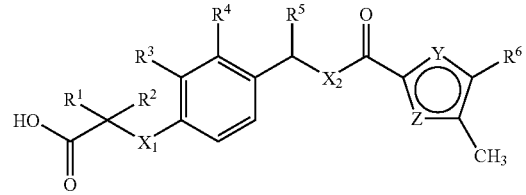

Wherein  
$X_1$ represents O or S;  
$R^1$ and $R^2$ are independently H or $C_{1-3}$ alkyl or $R^1$ and $R^2$ which are bonded to the same carbon atom may together with the carbon atom to which they are bonded form a 3–5 membered cycloalkyl ring;  
$R^3$ and $R^4$ independently represent H, halogen, —$CH_3$ and —$OCH_3$;  
$R^5$ represents H or $C_{1-6}$ alkyl  
$X_2$ represents NH, $NCH_3$ or O;  
One of Y and Z is N, and the other is O or S;  
$R^6$ represents phenyl or pyridyl (wherein the N is in position 2 or 3) and is optionally substituted by one or more halogen, $CF_3$, $C_{1-6}$ straight or branched alkyl (optionally substituted by halogen), with the provision that when $R^6$ is pyridyl, the N is unsubstituted.

6 Claims, No Drawings

OXAZOL/THIAZOL-DERIVATIVES ACTIVATORS OF THE HPPAR-ALPHA RECEPTOR

This application is filed pursuant to 35 U.S.C. § 371 as a United States National Phase Application of International Application No. PCT/EP02/05886 filed May 29, 2002, which claims priority from GB 0113231.5 filed May 31, 2001.

The present invention relates to certain novel compounds. In particular, the present invention relates to compounds that activate the alpha subtype of the human peroxisome proliferator activated receptor ("hPPAR alpha"). The present invention also relates to methods for preparing the compounds and methods for prevention or treatment of PPAR alpha mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e., currently there are no drugs on the market that are useful for raising HDL-c>40%). (Bisgaier, C. L.; Pape, M. E. Curr. Pharm. Des. 1998, 4, 53–70).

Syndrome X (including metabolic syndrome) is loosely defined as a collection of abnormalities including hyperinsuinlemia, obesity, elevated levels of trigycerides, uric acid, fibrinogen, small dense LDL-c particles, and plasminogen activator inhibitor 1 (PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARS) are orphan receptors belonging to the steroid/retinoid receptor superfamily of ligand-activated transcription factors. See, for example, Willson, T. M. and Wahli, W., Curr. Opin. Chem. Biol., (1997), Vol. 1, pp 235–241.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endocrin. Met* 291–296, 4 (1993)).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.) and WO99/04815 (Shimokawa et al.).

Fibrates are a class of drugs which may lower serum triglycerides 20–50%, lower LDL-c 10–15%, shift the LDL particle size from the more atherogenic small dense to normal dense LDL-c, and increase HDL-c 10–15%. Experimental evidence indicates that the effects of fibrates on serum lipids are mediated through activation of PPAR alpha. See, for example, B. Staels et al., *Curr. Pharm. Des.,* 1–14, 3 (1), (1997). Activation of PPAR alpha results in transcription of enzymes that increase fatty acid catabolism and decrease de-novo fatty acid synthesis in the liver resulting in decreased triglyceride synthesis and VLDL-c production/secretion. In addition, PPAR alpha activation decreases production of apoC-III. Reduction in apoC-III, an inhibitor of LPL activity, increases clearance of VLDL-c. See, for example, J. Auwerx et al., *Atherosclerosis*, (Shannon, Irel), S29–S37, 124 (Suppl), (1996). PPAR alpha ligands may be useful for the treatment of dyslipidemia and cardiovascular disorders, see Fruchart, J. C., Duriez, P., and Staels, B., *Curr. Opin. Lipidol.* (1999), Vol 10, pp 245–257.

According to a first aspect of the invention there is provided a compound of formula (I) and pharmaceutically acceptable salts, solvates and hydrolysable esters thereof:

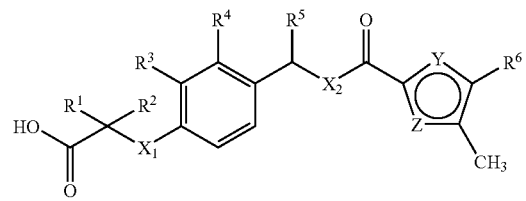

wherein $X_1$ represents O or S;

$R^1$ and $R^2$ are independently H or $C_{1-3}$ alkyl or $R^1$ and $R^2$ which are bonded to the same carbon atom may together with the carbon atom to which they are bonded form a 3–5 membered cycloalkyl ring;

$R^3$ and $R^4$ independently represent H, halogen, —$CH_3$ and —$OCH_3$;

$R^5$ represents H or $C_{1-6}$ alkyl $X_2$ represents NH, $NCH_3$ or O;

One of Y and Z is N, and the other is O or S;

$R^6$ represents phenyl or pyridyl (wherein the N is in position 2 or 3) and is optionally substituted by one or more halogen, $CF_3$, $C_{1-6}$ straight or branched alkyl (optionally substituted by halogen), with the provision that when $R^6$ is pyridyl, the N is unsubstituted.

In another aspect, the present invention discloses a method for prevention or treatment of a human PPAR alpha, gamma or delta ("hPPAR") mediated diseases or conditions comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, opithelial hyperproliferative diseases including eczema and psoriasis and contiditions associated with the lining and gut and regulation of appetite and food intake in subjects suffering from disorders such as obesity, bulimia, and anorexia nervosa. In particular, the compounds of this invention are useful in the treatment and prevention of cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

In another aspect, the present invention provides a method of treatment of a patent suffering from a hPPAR mediated disease or condition comprising the administration of a therapeutically effective amount of a compound of the invention.

As used herein, "a compound of the invention" means a compound of formula (I) or a pharmaceutically acceptable salt, solvate, or hydrolyzable ester thereof.

While hydrolyzable esters are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably $X_1$ represents O.
Preferably $R^1$ and $R^2$ are methyl
Preferably one of $R^3$ and $R^4$ represents H with $R^3$ and $R^4$ both representing H being more preferred.
Preferably $R^5$ represents H.
Preferably $X_2$ represents NH.
Preferably Z represents N.
Preferably Y represents S.
Preferably $R^6$ is phenyl, optionally substituted. Preferably $R^6$ is mono or disubstituted. Preferably when $R^6$ is pyridyl the N is in the 2 position. $R^6$ preferably is monosubstituted in the para position and is more preferably phenyl. A preferred substituent is F, $CF_3$, ethyl or methyl.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Preferably, the compounds of formula (I) are hPPAR agonists. The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARα in the binding assay described below, and which achieve at least 50% activation of the relevant PPAR relative to the appropriate indicated positive control in the transfection assay described below at concentrations of $10^{-5}$ M or less. More preferably, the compounds of this invention achieve 50% activation of at least one human PPAR in the relevant transfection assay at concentrations of $10^{-6}$ M or less. More preferably the compounds of the invention achieve 50% activation of at least one human PPAR in the relevant transfection assay at concentrations of $10^{-7}$M or less.

Preferably the compounds hPPARα agonists.

Most preferably, the compounds of formula (I) are selective hPPAR alpha agonists. As used herein, a "selective hPPAR alpha agonist" is a hPPAR alpha agonist whose $EC_{50}$ for PPAR alpha is at least 10 fold lower than its $EC_{50}$ for PPAR gamma and PPAR delta. Such selective compounds may be referred to as "10-fold selective." $EC_{50}$ is defined in the transfection assay described below and is the concentration at which a compound achieves 50% of its maximum activity. Most preferred compounds are greater than 100-fold selective hPPAR alpha agonists.

Preferred compounds of the invention include:
2-methyl-2-[4-{[(4-methyl-5-[4-ethylphenyl]thiazol-2yl-carbonyl)amino]methyl}phenoxy]propionic acid ethyl ester.
2-methyl-2-[4-{[(4-methyl-5-[4-fluorophenyl]thiazol-2-ylcarbonyl)amino]methyl}phenoxy]propionic acid ethyl ester.

More preferred compounds of the invention include:
2-methyl-2-[4-{[(4-methyl-5-[4-fluorophenyl]thiazol-2-ylcarbonyl)amino]methyl}phenoxy]propionic acid.

A particularly preferred compound of the invention is 2-methyl-2-[4-{[(4-methyl-5-[4-ethylphenyl]thiazol-2-yl-carbonyl)amino]methyl} phenoxy]propionic acid.

Those skilled in the art will recognize that stereocenters exist in compounds of formula (I). Accordingly, the present invention includes all possible stereoisomers and geometric isomers of formula (I) and includes not only racemic compounds but this invention is also intended to cover each of these isomers in their racemic, enriched, or purified forms. When a compound of formula (I) is desired as a single enantiomer, it may be obtained either by resolution of the final product or by stereospecific synthesis using an optically active catalyst or a catalytic system with optically active ligands or isomerically pure starting material or any convenient intermediate. Resolution of the final product, an intermediate or a starting material may be effected by any suitable method known in the art. See, for example, Stereochemistry of Carbon Compounds by E. L. Eliel (Mcgraw Hill, 1962) and Tables of Resolving Agents by S. H. Wilen. Additionally, in situations where tautomers of the compounds of formula (I) are possible, the present invention is intended to include all tautomeric forms of the compounds. In particular, in many of the preferred compounds of this invention the carbon atom to which $R^1$ and $R^5$ are bonded is chiral. In some of these chiral compounds the activities at the various PPAR receptors varies between the S and R isomers. Which of these isomers is preferred depends on the particular desired utility of the compound. In other words, even with the same compound, it is possible that the S isomer will be preferred for some uses, while the R isomer will be preferred for others.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma agonists (for example thiazolidinediones such as e.g. Pioglitazone and Rosiglitazone). The compounds may also be used in combination with antihypertensive agents such as calcium channel antagonists and ACE inhibitors. The invention thus provides in a further aspect the use of a combination comprising a compound of formula (I) with a further therapeutic agent in the treatment of a hPPAR alpha mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

Compounds of this invention may be conveniently prepared by a general process wherein a moiety like (A) is coupled to an acid (B) using a peptide coupling reaction or by acylation of (A) with an ester (C). R in formula (C) is preferably $C_{1-6}$alkyl. Note this synthesis is preferably carried out with the acid group of moiety A protected by R. Thus while R can be H, preferably R is 1–6 alkyl which can be hydrolyzed off to give an acid of Formula (I), or if readily hydrolyzable, the resulting ester can be administered. Compounds of (A), (B) and (C) may be synthesised, eg as demonstrated in the Examples below. Intermediates of this type may be commercially available or their preparation will be apparent to a person skilled in the art, eg by analogous methods to those described below.

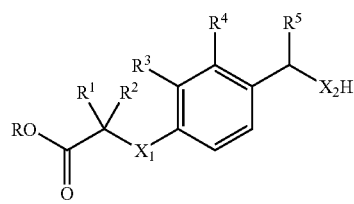

A

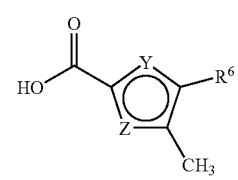

B

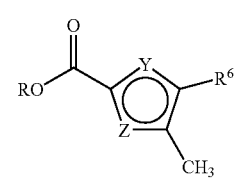

C

A preferred synthesis of (A) when $X_1$ is O and $X_2$ is NH ($R^1, R^2$ are methyl and $R^3, R^4, R^5$ are H) is:

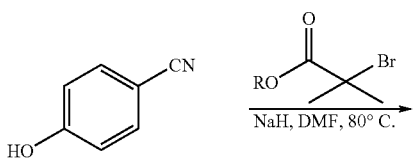

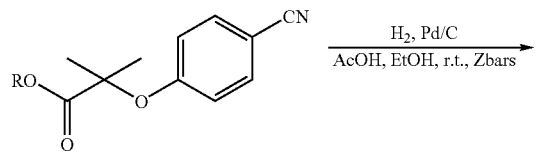

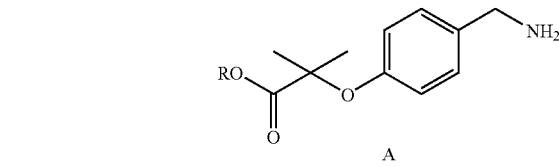

A

Note that this synthesis may be carried out with the carboxylic acid B (method A) or with the ester C (method B). For example, when $X_1$ is O, $X_2$ is NH, Y is S, Z is N, $R^1=R^2$=methyl, $R^3=R^4=R^5$=H and $R^6$ is 4-Et-phenyl:

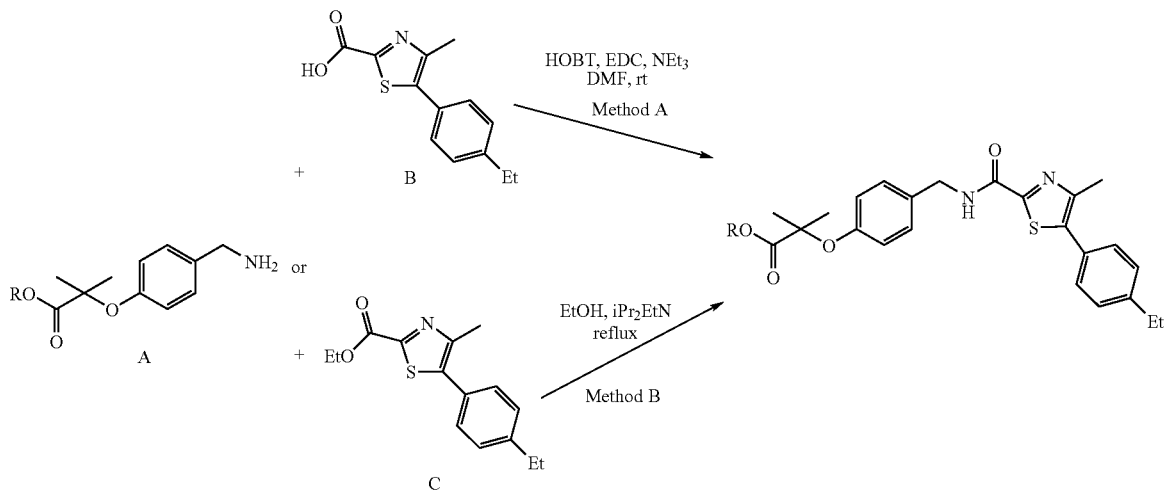

When $X_1$ and $X_2$ are O, compounds of formula (1) may be prepared by reaction of compounds of formula (B) with compounds of formula (A) with DIC/DMAP/NEt$_3$.

The invention is further illustrated by the following intermediates and examples which should not be construed as constituting a limitation thereto.

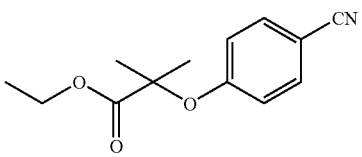

Intermediate 1:

To a solution of 212.8 g (1.79 moles) of para hydroxybenzonitrile in 1.7 L of DMF (8 vol.) cooled to 15° C. were added portionwise 121 g (3.04 mol., 1.7 equiv.) of NaH dispersed in parafin (60%) in 35 minutes. After return to room temperature, the mixture was stirred for 30 minutes and 393 mL (2.68 mol., 1.5 equiv.) of ethyl bromoisobutyrate were slowly added in 1 hour. During the addition, the inert temperature was maintained below 25° C. by cooling because a slightly exothermic effect occurred. The mixture was stirred overnight at room temperature and heated at 80° C. for 2 hours. After cooling at a temperature below 20° C., the excess of sodium hydride was destroyed by the addition of 600 ml of 1N sodium hydroxide solution. The aqueous solution was extracted 3 times with 1 L of ethyl ether. The combined organic layers were washed twice with 200 ml of 1N sodium hydroxide solution (to eliminate traces of the para hydroxybenzonitrile) and 500 ml of brine. After drying on magnesium sulphate, filtered and concentrated to dryness, the oily residue was decanted and 33.5 g of the parafin oil was removed (the upper layer). The 189.9 g of the oily residue was estimate to be mixed with 14.9 g of residual parafin oil. Crude intermediate 1 was used without further purification. The yield is estimated to be about 42% (about 175 g).

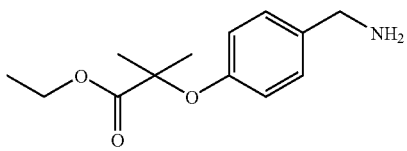

Intermediate 2:

In a hydrogenator of 1 L, a mixture of 59.3 g of intermediate 1 (0.254 mol. (maximum), 43.6 ml (0.762 mol., 3 equiv.) of glacial acetic acid and 6 g (10% w/w) of Pd/C 10% in 250 ml of ethyl alcohol was hydrogenated over 2 bars of hydrogen and at room temperature. The reaction stopped after 8 hours when 8.7 L of hydrogen were absorbed (theoretical volume: 11.4 L). After filtration of the catalyst, the solution was evaporated to dryness to give the acetic salt of intermediate 2 (oily residue). The residue was poured in 300 ml of water (pH=5) and the aqueous layer was extracted twice with 200 ml of cyclohexane. During this operation, a gummy solid appeared which is left in the aqueous layer (probably a part of the acetic salt). After addition of 400 ml of ethyl acetate, the biphasic mixture was cooled to 15° C. and treated with 500 ml of 1N NaOH solution (to pH=12). After decantation, the aqueous layer was extracted twice with 400 ml of ethyl acetate. The combined organic layer was washed with 200 ml of brine. The organic layer was dried on magnesium sulphate, filtered and evaporated in vacuo to give 35.5 g of crude intermediate 2 (yellow oil, 58.9% yield) which were used in the next step without further purification (LC-MS purity=about 90%).

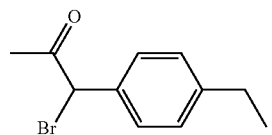

Intermediate 3:

To a solution of 200 g (1.23 mol, Avocado) of 4-ethylphenylacetone in 800 ml of acetic acid, were added at 10–12°

C. dropwise 61.8 ml (1 equiv.) of bromine in 600 ml of acetic acid for 2 h. At the end of the addition, the mixture was stirred for 5 min and then treated with water (2 L). After cooling 100 g of Na$_2$SO$_3$ were added and the resulting mixture was stirred for 1 h at room temperature. The biphasic mixture was decanted and the aqueous layer extracted twice with 1 L of CH$_2$Cl$_2$. The whole organic layer was washed with 1 L of water and dried over Na$_2$SO$_4$. After filtration and concentration to dryness, 288 g of a brown oil was obtained (97% yield).

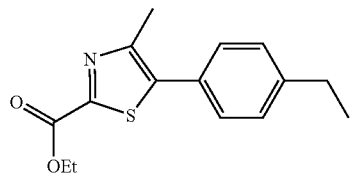

Intermediate 4:

To a solution of 288 g (1.19 mol.) of the intermediate 3 in 2.9 L of ethyl alcohol were added 158.8 g (1 equiv., Acros) of ethyl thiooxamate. The solution was stirred at room temperature for 1 hours and was then refluxed for 1 h. After evaporation of the ethyl alcohol, the dark residue was diluted with 1 L of water and extracted with 3×500 ml of CH$_2$Cl$_2$. The organic layer was washed twice with 500 ml of water. After drying over Na$_2$SO$_4$ and evaporation under reduced pressure, 32.6 g of a crude oil were obtained. Purification by chromatography with 98:2 petroleum ether/ethyl acetate gave 30.9 g of intermediate 4 as a grey oil (60.6% yield).

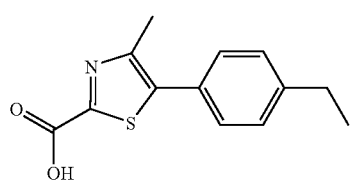

Intermediate 5:

To a solution of 0.6 g of intermediate 4 (22 mmol) in 10 ml of ethyl alcohol were added 6.5 ml (13 equiv.) of NaOH 1N. The mixture was stirred at reflux for 30 min and then was concentrated under reduced pressure. The residue was diluted in water and extracted with ethyl ether. The aqueous layer was acidified with HCl 1N and extracted with CH$_2$Cl$_2$. The organic layer was dried over Na$_2$SO$_4$, filtered and evaporated in vacuo to give 0.4 g of intermediate 5 as a yellow solid (73.6% yield).

MS m/z 248 (M+1)

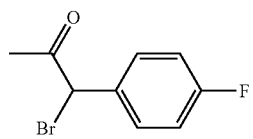

Intermediate 6:

To a solution of 10 g (65.8 mmol, Aldrich) of 4-fluorophenylacetone in 100 ml of benzene, 10.5 g (1 equiv.) of bromine were added dropwise at 10° C. The reaction mixture was stirred at room temperature for 1 h. At the end of the reaction, azote was bubbled into the reaction mixture. The mixture was concentrated under vacuum and the resulting oil was distilled to give 9 g of an oil (yield=59%). Eb=130–135° C. at 20 mm Hg.

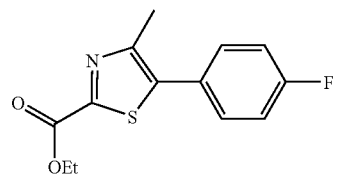

Intermediate 7:

To a solution of 1 g (4.33 mmol.) of the intermediate 6 in 30 ml of ethyl alcohol was added 0.54 g (1 equiv., Acros) of ethyl thiooxamate. The solution was stirred at reflux overnight. The solution was concentrated in vacuo and the oily residue was diluted with water and extracted with CH$_2$Cl$_2$. The organic layer was washed with brine, dried over Na$_2$SO$_4$ and evaporated under reduced pressure. The resulting crude oil was chromatographied with 99:1 dichloromethane/methanol to give 0.26 g of intermediate 7 as a brown solid (yield=22.6%). m.p: 69–70° C.

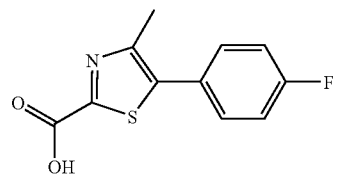

Intermediate 8:

To a solution of 1.5 of intermediate 7 (5.66 mmol) in 50 ml of ethyl alcohol were added 20 ml of NaOH 1N. The mixture was stirred at reflux for 30 min and then was concentrated under reduced pressure. The residue was diluted in water and extracted with ethyl ether. The aqueous layer was acidified with HCl 1N and extracted with CH$_2$Cl$_2$. The organic layer was dried over Na$_2$SO$_4$, filtered and evaporated to dryness to give intermediate 7 as an off-white solid (0.81 g, 60% yield). m.p: 140° C.

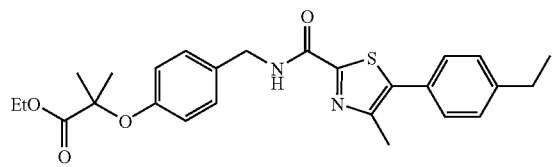

EXAMPLE 1

2-methyl-2-[4-{[(4-methyl-5-[4-ethylphenyl]thiazol-2-ylcarbonyl)amino]methyl}phenoxy]propionic Acid Ethyl Ester Method A To a solution of 250 mg of intermediate 2 (1 mmol) in 10 ml of dichloromethane were added 174 mg of HOBT(1.3 equiv.), 284 mg of EDC (1.3 equiv.), 260 mg of intermediate 5 (1 equiv.) and 130 mg of triethylamine (1.3 equiv.). The reaction mixture was stirred at room temperature for 2 days. The mixture was treated with diluted NaOH and extracted with CH$_2$Cl$_2$. The organic layer was washed with diluted HCl, water and dried over Na$_2$SO$_4$. After evaporation in vacuo, the resulting crude oil was purified by chromatography with 99:1 dichloromethane/methanol to give 100 mg of example 1 as an oil (21.5% yied).

Method B

To a solution of 26.93 g (97.9 mmol) of intermediate 4 and 46.5 g (2 equiv.) of intermediate 2 in 300 ml of ethyl alcohol, was added 85.3 ml (5 equiv.) of di-isopropylethylamine. The reaction mixture was stirred under reflux for 2 days. To complete the reaction, 23.5 g (1 equiv.) of intermediate 2 in 50 ml of ethyl alcohol were added. The reaction mixture was stirred under reflux for 7 h and one more equivalent of intermediate 2 (23.5 g) was added. The mixture was maintained at reflux for 24 h. The reaction was concentrated in vacuo, the residue was diluted with water and basified with NaOH 1N. The aqueous layer was extracted with ethyl acetate (3×300 ml) and the organic layer washed with HCl 1N, a saturated solution of NaHCO$_3$ and brine. The whole organic layer was dried over MgSO$_4$, filtered and evaporated to dryness. The resulting crude oil was chromatographied with 80:20 petroleum ether/ethyl acetate to give example 1 as a colourless oil (40.9 g, yield=89.6%).

$^1$H NMR (CDCl3): δ 7.57 (m, 1H), 7.29 (d, 2H), 7.15–7.21(m, 4H), 6.75 (d, 2H), 4.50 (d, 2H), (4.16 (q, 2H), 2.62 (q, 2H), 2.40 (s, 3H), 1.52 (s, 6H), 1.20 (s, 3H), 1.10 (s, 3H).

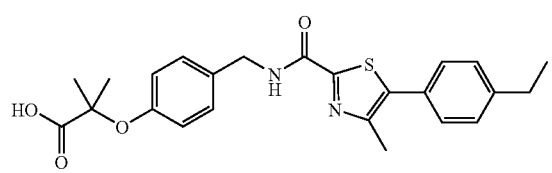

EXAMPLE 2

2-methyl-2–[4-{[(4-methyl-5-[4-ethylphenyl]thiazol-2-ylcarbonyl) amino]methyl}phenoxy]propionic Acid To a solution of 100 mg (0.21 mmol.) of example 1 in 5 ml of ethyl alcohol was added 0.63 ml (3 equiv.) of NaOH (1N). The solution was stirred at reflux for 30 min. After removal of the solvent under reduced pressure, the residue was diluted with water and acidified with HCl 1N to pH=1. The aqueous layer was extracted with CH$_2$Cl$_2$ and dried over Na$_2$SO$_4$. After filtration and concentration to dryness, the oily residue was organized with a mixture of with CH$_2$Cl$_2$ and pentane. The solid was filtered and dried in vacuum oven to give example 2 as a white solid (50 mg, yield=53.2%), mp=159–162° C. MS m/z467 (M+1).

$^1$H NMR (CDCl3): δ 7.57 (m, 1H), 7.18 (d, 2H), 7.10 (d, 2H), 6.74 (d, 2H), 4.41 (d, 2H), 2.52 (q, 2H), 2.30 (s, 3H), 1.43 (s, 6H), 1.10 (s, 3H).

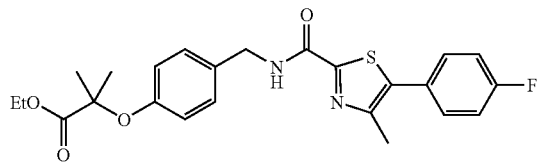

EXAMPLE 3

2-methyl-2-[4-{[(4-methyl-5-[4-fluorophenyl]thiazol-2-ylcarbonyl)amino]methyl}phenoxy]propionic Acid Ethyl Ester To a solution of 320 mg of intermediate 2 (1.35 mmol) in 30 ml of dimethylformamide were added 240 mg of HOBT (1.3 equiv.), 340 mg of EDC (1.3 equiv.), 320 mg of intermediate 7 (1 equiv.) and 0.25 ml of triethylamine (1.3 equiv.). The reaction mixture was stirred at room temperature overnight. The mixture was evaporated under reduced pressure, diluted with water and extracted with with CH$_2$Cl$_2$. The organic layer was washed with water and brine, dried over Na$_2$SO$_4$ and evaporated in vacuo. The resulting crude oil was purified by chromatography with 99:1 dichloromethane/methanol to give 330 mg of example 1 as a white solid (yied=53.5%). m.p: 97° C. MS m/z 457 (M+1).

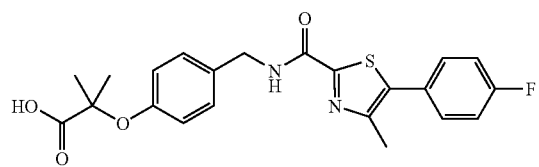

EXAMPLE 4

2-methyl-2-[4-{[(4-methyl-5-[4-fluorophenyl]thiazol-2-ylcarbonyl)amino]methyl}phenoxy]propionic Acid To a solution of 310 mg (0.68 mmol.) of example 3 in 25 ml of tetrahydrofuran were added 2 ml (5 equiv.) of LiOH 1N. The solution was stirred at 50° C. for 30 min. To complete the reaction 2 ml of NaOH 1N were added and the solution was stirred 1 h at 50° C. After removal of the solvent under reduced pressure, the residue was diluted with water and the aqueous layer was extracted with diethylether. The aqueous layer was treated with 5.4 ml of HCl N and extracted with diethylether. The organic layer was dried over Na$_2$SO$_4$, filtered and evaporated in vacuo to obtain a solid which was recrystallized from diisopropylether to give 230 mg of example 4 as a white solid (72% yield), mp=122° C. MS m/z 429(M+1).

Binding Assay:

Compounds were tested for their ability to bind to hPPAR gamma hPPARalpha or PPARdelta using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand ($^3$H-BRL 49653 for PPARgamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002) and labelled GW 2433 for PPAR delta (see Brown, P. J et al. *Chem. Biol.* 1997, 4, 909–918 for the structure and synthesis of this ligand) and variable concentrations of test compound, and after equilibration the radioactivity bound to the beads was measured by a scintillation counter. The amount of nonspecific binding, as assessed by control wells containing 50 µM of the corresponding unlabeled ligand, was subtracted from each data point. For each compound tested, plots of ligand concentration vs. CPM of radioligand bound were constructed and apparent $K_1$ values were estimated from nonlinear least squares fit of the data assuming simple competitive binding. The details of this assay have been reported elsewhere (see, Blanchard, S. G. et. al. *Development of a Scintillation Proximity Assay for Peroxisome Proliferator-Activated Receptor gamma Ligand Binding Domain. Anal. Biochem.* 1998, 257, 112–119).

Transfection Assay:

The following ligands were prepared for the transfection assay described below:

(i) 2-{2-methyl-4-[({4-methyl-2-[4-(trifluoromethyl)phenyl]-1,3-thiazol-5-yl}methyl)sulfanyl]phenoxy}acetic Acid.

This compound was used as a PPARdelta reference in the transfection assays described below and was prepared according to the method reported in WO200100603-A1

(ii  2-methyl-2-[4-{[(4-methyl-2-[4-trifluoromethylphenyl]-thiazol-5-yl  carbonyl)amino]methyl}phenoxy]pronpionic Acid.

This compound was used as a PPAR alpha reference in the transfection assay described below and was prepared according to method reported in WO200140207-A1 (and reproduced below)

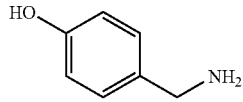

Intermediate (a):

Same procedure as Stout, D. M. *J. Med. Chem.* 1983, 26(6), 808–13. To 4-methoxybenzyl amine (25 g, 0.18 mol; Aldrich) was added 46% HBr in H$_2$O (106 ml, 0.9 mol; Aldrich). The reaction was refluxed overnight, then the reaction cooled to 0° C. and neutralized to pH7 slowly with KOH$_{(s)}$. The reaction is allowed to stir for ~30 min, then the solid filtered and dried. The solid redisolved in hot MeOH, filtered and the solution cooled to afford 19 g (85%) intermediate 1. $^1$H NMR (DMSO-d$_6$): δ 8.0 (bs, 1H), 7.2 (d, 2H), 6.75 (d, 2H), 3.85 (s, 2H), 3.50 (bs, 2H).

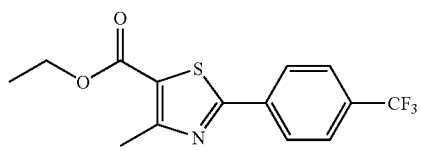

Intermediate (b):

A solution of ethyl 2-chloroacetoacetate (35.3 g, 29.7 mL, 0.21 mol) and 4-(trifluoromethyl)thiobenzamide (44 g, 0.21 mol) in EtOH (300 mL) was refluxed overnight. After cooling to room temperature the solvent removed in vacuo. The final product (intermediate (b)) was recrystallized from a minimum of MeOH to afford 40 g (59%) of final product as a white solid. $^1$H NMR (CDCl$_3$): δ 8.10 (d, 2H), 7.70 (d, 2H), 4.40 (q, 2H), 2.80 (s, 3H), 1.4 (t, 3H).

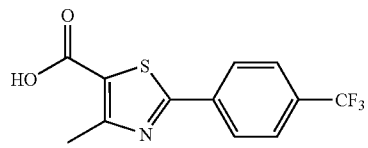

Intermediate (c):

To intermediate (b) (1.84 g, 5.8 mmol) in THF was added 1N LiOH (6 mL, 6 mmol) and the reaction stirred at rt. After ~3 h, the reaction neutralized with 1N HCl, extracted 3×100 mL EtOAc, dried over Na$_2$SO$_4$, filtered and the solvent removed under vaccum to afford 1.5 g (89%) intermediate (b) as a white solid. $^1$H NMR (DMSO-d$_6$): δ 13.55 (bs, 1H), 8.25 (d, 2H), 7.95 (d, 2H), 2.75 (s, 3H).

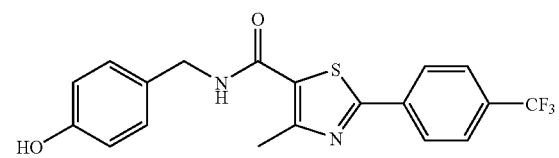

Intermediate (d):

To intermediate (c) (1 g, 7 mmol) in CH$_2$Cl$_2$/DMF (1:1) was added HOBT (565 mg, 4.2 mmol; Aldrich), EDC (800 mg, 4.2 mmol; Aldrich) and intermediate 1 (860 mg, 7 mmol). The reaction stirred at rt for 18 h. The solvent removed in vacuo, treated with H$_2$O and extracted 3×100 mL CH$_2$Cl$_2$. The organic phases combined and washed with 1N HCl, dried over Na$_2$SO$_4$, filtered and evaporated to afford a mixture (N-substituted and N,O-substituted). The mixture disolved in MeOH and treated with 1N NaOH. The reaction stirred 18 h at 50° C. The solvent removed in vacuo, dissolved in CH$_2$Cl$_2$, washed with H$_2$O, and dried over Na$_2$SO$_4$. The solvent evaporated the residue chromatographed (CH$_2$Cl$_2$/MeOH: 99/1) to afford 610 mg (47%) of intermediate 6 as a white solid. $^1$H NMR (DMSO-d$_6$): 9.30 (s, 1H), 8.80 (t, 1H), 8.20 (d, 2H), 6.70 (d, 2H), 4.35 (d, 2H), 2.6 (s, 3H).

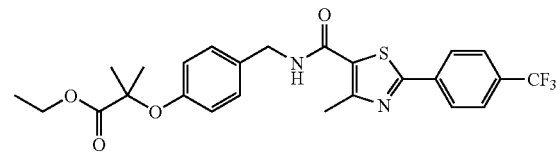

Intermediate (e):

2-methyl-2-[4-{[(4-methyl-2-[4-trifluoromethylphenyl] thiazol-5-ylcarbonyl)amino]methyl}phenoxy]propionic Acid Ethyl Ester To intermediate (d) (710 mg, 1.81 mmol) in DMF (50 mL) was added the K$_2$CO$_3$ (275 mg, 1.99 mmol) followed by the ethyl 2-bromo-2-methylpropanate (280 µL, 1.91 mmol; Aldrich) and the reaction heated to 80° C. After 18 h, the reaction cooled to rt and the solvent removed in vacuo. The residue treated with water (200 mL), extracted 3×50 mL CH$_2$Cl$_2$, dried over Na$_2$SO$_4$, filtered and the solvent removed under vaccum. The residue was chromatographed (CH$_2$Cl$_2$/MeOH: 99/1). To afford 680 mg (77%) of Example 1 as a clear oil. $^1$H NMR(CDCl$_3$): δ 7.95 (d, 2H), 7.60 (d, 2H), 7.15 (d, 2H), 6.75 (d, 2H), 6.05 (t 1H), 4.45 (d, 2H), 4.15 (q, 2H), 2.65 (s, 3H), 1.50 (s, 6H), 1.20 (t, 3H).

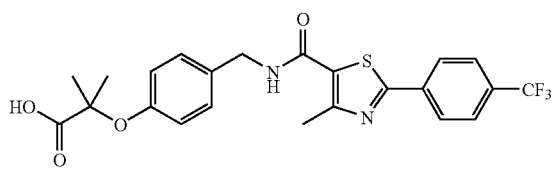

2-methyl-2-[4-{[(4-methyl-2-[4-trifluoromethylphenyl]-thiazol-5-ylcarbonyl)amino]methyl}phenoxy]propionic Acid To Intermediate (e) (680 mg, 1.39 mmol) in MeOH was added 1N NaOH (1.6 mL, 1.6 mmol) and the reaction stirred at 60° C. After 18 h, the reaction cooled to rt and the solvent evaporated. The residue treated with 1N HCl, extracted 3×20 mL THF and the solvent removed under vacuum. 500 mg (75%) The title compound was precipitated as a white solid from a minimum CH$_2$Cl$_2$ and pentane. mp: changes the form between 60–70° C.; LC/MS (m/z): 477.22 (100%, AP−), 479.12 (100%, AP+); anal. C$_{23}$H$_{21}$F$_3$N$_2$O$_4$S: C, 5.71 (57.73), H, 4.56 (4.42), N, 5.77 (5.85), S, 6.15 (6.70).

(iii) 5-{4-[2-(Methyl-pyridin-2-yl-amino)-ethoxy]-benzyl}-thiazolidine-2.4-dione This compound was used as a PPAR gamma reference in the transfection assay described below and was prepared according to method reported in *J. Med. Chem.* 1994, 37(23), 3977

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., *An antidiabetic thiazolidinedione is a high affinity ligand for peroxisome proliferator-activated receptor gamma (PPARgamma)*, J. Biol. Chem., 1995, 270, 12953–6. The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with0 a reporter construct containing five copies of the GAL4 DNA binding site driving expression of secreted placental alkaline phosphatase (SPAP) and β-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-alactosidase activity. Alkaline phosphatase activity was corrected for transfection efficiency using the β-galactosidase activity as an internal standard (see, for example, Kliewer, S. A., et. al. *Cell* 83, 813–819 (1995)). Rosiglitazone (BRL 49653) was used as a positive control in the hPPAR gamma assay. The positive control in the hPPAR alpha assays was 2-(2-methyl-3-[3-{3-(4-cyclohexylamino)-[6-(4-fluorophenylpiperazin-1-yl)][1,3,5]triazin-2-ylamino}propyl]phenylthio)-2-methylpropionic acid. The positive control for PPAR delta assays was 2-{2-methyl-4-[({4-methyl-2-{trifluoromethyl)phenyl]-1,3-thiazol-5-yl}methyl)sulfanyl]phenoxy}acetic acid.

Activities in three hPPAR subtypes are reported in the table below for the most preferred compounds and are expressed in nanomolar.

| Example | EC50 nM HPPARα | EC50 nM HPPARδ | EC50 nM HPPARγ |
|---------|----------------|----------------|----------------|
| 2 | 5 | 8740 | 700 |
| 4 | 61 | 10000 | 5882 |

What is claimed is:

1. A compound of formula (I) or a pharmaceutically acceptable salt, solvate or hydrolysable ester thereof

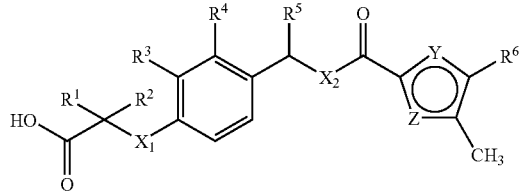

Wherein
X$_1$ represents O;
R$^1$ and R$^2$ are methyl;
R$^3$ and R$^4$ are both H;
R$^5$ represents H;
X$_2$ represents NH,
Z is N and Y is S;
R$^6$ represents phenyl and is optionally monosubstituted in the para position with halogen, —CF$_3$, or C$_{1-6}$ straight or branched alkyl.

2. A compound as claimed in claim 1 which is a selective hPPAR alpha agonist.

3. A compound selected from the group consisting of:
2-methyl-2-[4-{[(4-methyl-5-[4-ethylphenyl]thiazol-2 ylcarbonyl)amino]methyl}phenoxy]propionic acid ethyl ester, 2-methyl-2-[4-([(4-methyl-5-[4-fluorophenyl]thiazol-2-ylcarbonyl)amino]methyl}phenoxy]propionic acid ethyl ester, 2-methyl-2-[4{[(4-methyl-5-[4-fluorophenyl]thiazol-2-ylcarbonyl)amino]methyl}phenoxy]propionic acid, and 2-methyl-2-[4{[(4-methyl-5-[4-ethylphenyl]thiazol-2-ylcarbonyl)amino]methyl}phenoxy]propionic acid.

4. 2-methyl-2-[4{[(4-methyl-5-[4-ethylphenyl]thiazol-2-ylcarbonyl)amino]methyl}phenoxy]propionic Acid.

5. A pharmaceutical composition comprising a compound according to claim 1, and pharmaceutically acceptable diluent or carrier. in a patient comprising the administration of a therapeutically effective amount of a compound according to claim 1.

6. A compound sa claimed in claim 1, of the structure

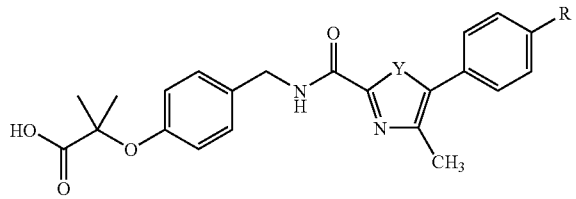

wherein R is $C_{1-6}$ straight or branched alkyl.

* * * * *

UNITED STATES PATENT AND TRADEMARK OFFICE
CERTIFICATE OF CORRECTION

| | | |
|---|---|---|
| PATENT NO. | : 7,157,479 B2 | Page 1 of 1 |
| APPLICATION NO. | : 10/478936 | |
| DATED | : January 2, 2007 | |
| INVENTOR(S) | : Gellibert | |

It is certified that error appears in the above-identified patent and that said Letters Patent is hereby corrected as shown below:

In the Claims:

Claim 5 (Column 19, Lines 8-12) should read as follows:

5. A pharmaceutical composition comprising a compound according to claim 1, and a pharmaceutically acceptable dilutent or carrier.

Claim 6 (Column 20, Line 1) should read as follows:

6. A compound as claimed in claim 1, of the structure

Signed and Sealed this

Fifth Day of June, 2007

JON W. DUDAS
*Director of the United States Patent and Trademark Office*